United States Patent [19]

Narayanan

[11] Patent Number: 5,326,789
[45] Date of Patent: Jul. 5, 1994

[54] WATER-BASED MICROEMULSIONS OF A TRIAZOLE FUNGICIDE

[75] Inventor: Kolazi S. Narayanan, Palisades Park, N.J.

[73] Assignee: ISP Investments Inc., Wilmington, Del.

[21] Appl. No.: 964,803

[22] Filed: Oct. 22, 1992

Related U.S. Application Data

[63] Continuation-in-part of Ser. No. 654,250, Feb. 12, 1991, abandoned, which is a continuation-in-part of Ser. No. 546,014, Jun. 28, 1990, Pat. No. 5,156,666, which is a continuation-in-part of Ser. No. 505,030, Apr. 5, 1990, Pat. No. 5,160,528, which is a continuation-in-part of Ser. No. 448,707, Dec. 11, 1989, Pat. No. 5,071,463.

[51] Int. Cl.$^5$ .................. A01N 25/00; A01N 43/64
[52] U.S. Cl. ................... 514/788; 514/383; 514/937; 514/938; 514/942
[58] Field of Search .............. 71/79, 86, 88, 93, 94, 71/100, 105, 107, 118; 514/383, 384, 788, 937, 938, 942; 504/189, 194, 229, 235, 306, 307, 342, 116

[56] References Cited

U.S. PATENT DOCUMENTS 4,840,663  6/1989  Quadranti et al. .............. 71/93

Primary Examiner—Marianne M. Cintins
Assistant Examiner—K. Weddington
Attorney, Agent, or Firm—Walter Katz; Marilyn J. Maue; Joshua J. Ward

[57] ABSTRACT

Clear, stable, efficacious, aqueous microemulsions of an active triazole fungicide, e.g. penconazole, optionally with another agriculturally active chemical, are provided herein. The aqueous microemulsions are obtained by providing an inert matrix composition comprising a defined mixture of nonionic surfactants, including a $C_6$–$C_{18}$ alkylpyrrolidone, e.g. octylpyrrolidone, an alkylphenol ethoxylated alcohol having an HLB $\geq$ 6, preferably 10–20, e.g. nonylphenol ethoxylated alcohol with 9 EOs, and an anionic surfactant selected from a salt of dodecyl sulfate, dodecylbenzene sulfonate, dodecyltoluene sulfonate and lignin sulfonate, preferably sodium dodecyl sulfate, and water, optionally with a $C_1$–$C_4$ alkylpyrrolidone, e.g. N-methylpyrrolidone, and water. The inert matrix composition is admixed with a triazole fungicide, present in a $C_1$–$C_4$ alkylpyrrolidone, if not already present in the inert matrix composition, to form a microemulsion concentrate. Upon dilution with water, a stable, aqueous microemulsion is formed characterized by having a high loading of triazole fungicide e.g. 1–25% (before dilution), preferably about 14%.

15 Claims, No Drawings

WATER-BASED MICROEMULSIONS OF A TRIAZOLE FUNGICIDE

CROSS-REFERENCE TO RELATED U.S. PATENT APPLICATIONS

This application is a continuation-in-part of application Ser. No. 654,250, filed Feb. 12, 1991, now abandoned which, in turn, is a continuation-in-part of application Ser. No. 546,014, filed Jun. 28, 1990, now U.S. Pat. No. 5,156,666 which, in turn, is a continuation-in-part of application Serial No. 505,030, filed Apr. 5, 1990, now U.S. Pat. No. 5,160,518 which, in turn, is a continuation-in-part of application Ser. No. 448,707, filed Dec. 11, 1989 now U.S. Pat. No. 5,071,463, (hereinafter, collectively referred to as the Parent Applications) the contents of all of which are incorporated herein by reference.

BACKGROUND OF THE INVENTION

1. Field of the Invention

This invention relates to a delivery system for agriculturally active chemicals, and, more particularly, to an inert matrix composition, a microemulsion concentrate and an aqueous microemulsion of a triazole-type fungicide.

2. Definitions

As used herein, the following terms have the meanings indicated:

(a) "Microemulsion" means an oil-in-water or water-in-oil, transparent thermodynamically stable dispersion of two or more immiscible liquids wherein the dispersed phase consists of small droplets with diameters in the range of about 10 to 100 millimicrons. Such microemulsions are clear and contain at least about 80% by weight water, and are intended for end-use applications.

(b) "Macroemulsion" means an emulsion of water-in-oil or oil-in-water wherein the interior phase is in the form of visually discernable droplets and the overall emulsion is cloudy, and wherein the droplet diameter is greater than about 100 millimicrons.

(c) "Clear" or "Transparent" as applied to a microemulsion means that the composition appears as a single phase without any particulate or colloidal material or a second phase being present when viewed by the naked eye.

(d) "Substantially Insoluble" or "Insoluble" means that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.

(e) "High Degree of Loading" in a microemulsion concentrate means an agriculturally active ingredient content of at least about 5 percent by weight.

(f) The term "Agriculturally Active Chemical or Ingredient" (AAC) means compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, synergists, i.e., compounds which when used in conjunction with other AAC's enhance their activity and the like, as well as any other chemicals having properties which are suitable for agricultural uses in terms of application to plants or domestic uses for controlling insects and pests.

(g) "Triazole-Type Fungicide" is an AAC such as:

PENCONAZOLE

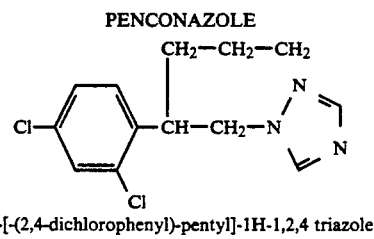

1-[-(2,4-dichlorophenyl)-pentyl]-1H-1,2,4 triazole

PROPICONAZOLE

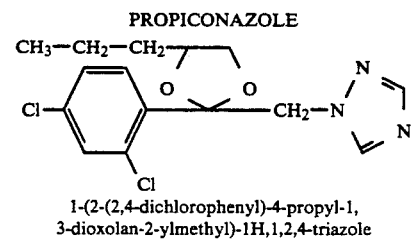

1-(2-(2,4-dichlorophenyl)-4-propyl-1, 3-dioxolan-2-ylmethyl)-1H,1,2,4-triazole

TRIADIMEFON

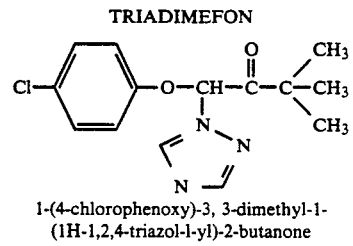

1-(4-chlorophenoxy)-3, 3-dimethyl-1-(1H-1,2,4-triazol-1-yl)-2-butanone

Other representative triazole fungicides include triadimenonol, bitertanol, Bayhwg 1608, diclolutrazol, hexaconazole, diniconazole, San 619F, flusilazol and myclobutanil.

(h) "Inert Matrix Composition" (IMC)—a predetermined mixture of defined nonionic surfactants, optionally with an anionic surfactant, and/or with a $C_1$-$C_4$ alkylpyrrolidone, and water, which, upon admixture with a triazole-type fungicide, will form a clear, efficacious, microemulsion concentrate, which, when diluted, will provide an aqueous microemulsion which is stable at or below room temperature for an extended period of time.

(i) "Two-Part Microemulsion System" (TPMS)—as the first part, the IMC; as the second part, a triazole-type fungicide; and, wherein, optionally, up to 60% by weight of a $C_1$-$C_4$ alkylpyrrolidone, e.g. N-methylpyrrolidone, is present in said system as a component of either or both of said parts before admixture.

(j) "Microemulsion Concentrate" (MEC)—the admixture product of both parts of the TPMS.

(k) "Water-Based Microemulsion" (WBME) or "Aqueous Microemulsion" (AM)—The TPMS (1 part by weight) and dilution water (10–100,000 parts by weight).

(l) "Nonionic Surfactant"—Representative materials include:
  (1) N-alkylpyrrolidone (alkyl $C_6$-$C_{18}$) e.g. N-octylpyrrolidone (Surfadone LP-100 - ISP)

(2) Alkylphenol ethoxylated alcohol having an HLB ≧6, e.g. nonylphenol ethoxylated alcohol with 9 EOs -(Igepal CO-630)

(m) "Anionic Surfactant"—Representative materials include a metal salt of dodecyl sulfate, e.g. sodium dodecyl sulfate (SDS); dodecylbenzene sulfonate, dodecyl toluene sulfonate and lignin sulfonate.

(n) "Cosolvent"—An N-alkyl ($C_1$-$C_4$) pyrrolidone, e.g. N-methylpyrrolidone (NMR).

DESCRIPTION OF THE PRIOR ART

Agriculturally active chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into a macroemulsion (sometimes referred to herein as an emulsion), it is difficult to maintain the emulsified state. This, in turn, creates problems in maintaining a uniform formulation, particularly, when the formulation is diluted with water for application to the plants.

An attempt to provide concentrates of agriculturally useful chemicals for producing macroemulsions was disclosed in South African Patent Application No. 695,393, filed Jul. 25, 1969. This application was directed to the formulation of a concentrate substantially water-insoluble pesticides for agricultural use. The pesticides, either in oil or solid form, were mixed with pyrrolidones having a hydrogen or a lower alkyl group containing from 1 to 4 carbon atoms attached to the nitrogen atom of the pyrrolidone ring. The application disclosed that concentrated solutions of difficult to dissolve pesticides could be formulated and that such concentrates exhibited good stability. The concentrates utilized were those containing the pesticidal active ingredient, the particular lower alkyl pyrrolidone, a cosolvent which is usually a common organic solvent, such as, an aromatic including xylene, methylated and polyalkylated naphthalenes and aliphatic solvents, and a dispersing or emulsifying agent, such as, a surfactant, including polyoxyethylene alkylphenols, polyoxyethylene fatty esters, polyoxyethylene sorbitan fatty esters which may be blended with oil-soluble sulfonates, calcium and aminosulfonate salts, and the like.

However, this prior art did not offer a solution to the problem arising from the difficulty in maintaining the stability of the emulsion formed after the concentrate was diluted with water. Consequently, unless the diluted form of the concentrate was used immediately after emulsification, it was difficult to provide a stable diluted formulation for application to the plants, soil, pests, and the like.

In addition, for such agricultural uses, it is also desirable to avoid the use of toxic solvents, including those of Lists 1 and 2 of 40 C.F.R. 154.7 dated Apr. 22, 1987, which includes inerts of toxicological concern and solvents having high flash points, as well as to increase the amount of the agriculturally active material in the concentrate. Moreover, many organic solvents which have been used in the past, even those exhibiting relatively low toxicities, are not biodegradable and thus remain as a pollutant.

The Parent Applications referred to hereinabove have provided solutions to the problem of providing stable macroemulsions of insoluble agricultural chemicals in aqueous systems. This was accomplished by the use of long and short chain alkyl lactams for formation of emulsifiable concentrates of agricultural chemicals. Also see U.S. Patent application Ser. No. 257,596, filed Oct. 14, 1988, (now U.S. Pat. No. 5,093,031), the contents of which are incorporated herein by reference, which disclosed the use of long chain alkyl lactams to prepare emulsifiable concentrates of agriculturally active ingredients, e.g., herbicides, fungicides, pesticides, and the like, which on dilution with water, formed stable macroemulsions.

While these patent applications disclose the preparation of emulsions of a wide variety of agriculturally active chemicals which are normally highly insoluble in water, the emulsions produced from all of these prior art concentrates are macroemulsions. The macroemulsions which result from their dilution with water, while relatively stable, may, at some point in time, settle out into two phases or more.

It is desirable, however, to provide compositions which will deliver effective amounts of insoluble agriculturally active compound which exhibit improved stability with respect to the emulsion. In addition, it is desired to provide increased chemical stability for such agricultural compounds. Thus, certain agricultural compounds, notably, insecticides, are relatively chemically unstable in water and tend to hydrolyze after a short period of time. As a result, even short periods of increased chemical stability for such compounds are advantageous.

It is also desirable to increase the efficacy of a given agricultural compound relative to its loading content. It has been theorized that microemulsions can improve the efficacy of agriculturally active compounds relative to equivalent levels of the same compound in a macroemulsion composition. See Skelton, P. R., Munk, B. H., and Collins, H. M., "Formulation of Pesticide Microemulsions", *Pesticide Formulations and Application Systems;* 8th Volume, ASTM STP 980, D. A. Hovde and G. B. Beestman, Eds., American Society for Testing and Materials, Philadelphia, 1988. See also U.S. Pat. No. 3,954,967, and Canadian Patent 1025687. For a discussion of microemulsions, see *Microemulsions, Theory and Practice,* Leon M. Prince, Academic Press, (1977); and "Microemulsions-Properties Novel Chemistry" BH Robinson Chemistry in Britain 26 (1990), page 342.

SUMMARY OF THE INVENTION

Clear, stable, efficacious, aqueous microemulsions of an active triazole fungicide, e.g. penconazole optionally with another agriculturally active chemical, are provided herein, the aqueous microemulsions are obtained by providing an inert matrix composition comprising a defined mixture of nonionic surfactants, including a $C_6$-$C_{18}$ alkylpyrrolidone, e.g. octylpyrrolidone, an alkylphenol ethoxylated alcohol having an HLB $\geq 6$, e.g. an HLB of about 10-20, such as nonylphenol ethoxylated alcohol with 9 EOs, and an anionic surfactant selected from a salt of dodecyl sulfate, dodecylbenzene sulfonate, dodecyltoluene sulfonate and lignin sulfonate, preferably sodium dodecyl sulfate, and water, optionally with a $C_1$-$C_4$ alkylpyrrolidone, e.g. N-methylpyrrolidone, mixing the inert matrix composition with the triazole fungicide, in a $C_1$-$C_4$ alkylpyrrolidone, if it is not present in the inert matrix composition, to form a microemulsion concentrate, and diluting the microemulsion concentrate with water to form a stable, aqueous microemulsion characterized by having a high loading of triazole fungicide, e.g. 1-25% (before dilution).

DETAILED DESCRIPTION OF THE INVENTION

In accordance with the invention, the Inert Matrix Composition (IMC) comprises a predetermined mixture of nonionic surfactants, particularly about 5-30% of a $C_6$-$C_{18}$ alkylpyrrolidone (Surfadone LP-100), about 5-30% of an alkyl phenol ethoxylated alcohol having an HLB $\geq 6$, e.g. an HLB of 10-20, such as nonylphenol ethoxylated alcohol with 9 EOS, (Igepal-CO-630), and about 5-30% of an anionic surfactant, suitably a metal salt of a dodecyl sulfate, dodecyl benzene sulfonate, dodecyl toluene sulfonate or lignin sulfonate, preferably sodium dodecyl sulfate (SDS), optionally with 0-60% of a $C_1$-$C_4$ alkylpyrrolidone cosolvent, preferably N-methylpyrrolidone (NMP) and about 5-40% of water.

The Two-Part Microemulsion System (TPMS) comprises, as one part, the IMC, and, as a second part, the triazole fungicide, wherein the optional NMP cosolvent may be present in the second part herein as a solvent for the triazole, or in the IMC, or in both parts. Preferably the TPMS includes up to 60% by weight of NMP, and, most preferably, in the IMC.

The Microemulsion Concentrate (MEC) is obtained by mixing both parts of the TPMS. Suitably, the triazole is present in the MEC in a loading of about 1-25%, preferably about 14%.

EXPERIMENTAL PROCEDURES AND RESULTS

The Water-Based Microemulsions (WBME) of the invention can be prepared by alternative procedures (a) and (b) which are described below.

Procedure (a)

The IMC was prepared by mixing predetermined amounts of defined nonionic and anionic surfactants, optionally with NMP. Then the triazole fungicide, optionally dissolved in NMP, was added and the mixture was shaken until the triazole dissolved or the mixture became homogeneous, typically in about 30 minutes, which resulted in formation of an MEC. Then the MEC was diluted with a predetermined amount of water to form the WBME. Water for dilution was either deionized water or WHO standard hard water (342 ppm as $CaCO_3$ equivalent).

Procedure (b)

The IMC was added to a triazole fungicide dissolved in N-methylpyrrolidone to form the MEC, and dilution water was added to form the WBME.

The aqueous microemulsion compositions of the invention made according to procedures (a) and (b) below are summarized in TABLES 1 and 2, wherein the component amounts are in grams.

Typical MEC compositions, in wt. %, are shown in Table 1 below.

TABLE 1

|  | A | B | C | D | E |
|---|---|---|---|---|---|
| Penconazole | 14.0 | 14 | 14 | 14 | 13.72 |
| NMP | 9.7 | 30.0 | 5.7 | 4.6 | 10.81 |
| N-Octylpyrrolidone | 14.1 | 24.8 | 18 | 28 | 20.58 |
| Igepal CO-630 | 14.0 | 7.0 | 14 | 12 | 10.98 |
| SDS* | 14.0 | 7.0 | 14 | 12 | 12.73 |
| Water* | 34.3 | 17.2 | 34.3 | 29.4 | 31.18 |
|  | 100.0 | 100.0 | 100.0 | 100.0 | 100.0 |

(*from a 29% aqueous solution)

The MEC compositions are storage-stable in its aqueous condition; it may be diluted with water and stored until use, or diluted with water just before use. Upon dilution of the MEC with water, e.g. up to 200 times, a Water-Based Microemulsion (WBME), or simply, an Aqueous Microemulsion (AM) is formed, which contains from a few ppm to about 2% by weight of the triazole fungicide, preferably about 0.1%.

A typical dilution of 140 of the MEC composition (A above) results in a AM having penconazole concentration of 0.1% and a water content of 99.5%, which is a clear, stable, one phase, aqueous microemulsion.

Typical aqueous microemulsions (AM) prepared by dilution of MEC compositions (A-E) above by about 140 times are given in Table 2 below.

TABLE 2

|  | A' | B' | C' | D' | E' |
|---|---|---|---|---|---|
| Penconazole | 0.1 | 0.1 | 0.1 | 0.1 | 0.1 |
| NMP | 0.07 | 0.21 | 0.04 | 0.03 | 0.08 |
| N-Octyl-pyrrolidone | 0.1 | 0.18 | 0.13 | 0.10 | 0.15 |
| Igepal CO-630 | 0.1 | 0.05 | 0.10 | 0.09 | 0.08 |
| SDS | 0.1 | 0.05 | 0.10 | 0.09 | 0.09 |
| Water | 99.53 | 99.41 | 99.53 | 99.5 | 99.5 |
|  | 100.0 | 100.0 | 100.0 | 100.0 | 100.0 |

The MEC and AM compositions described in Tables 1 and 2 above were clear and stable for more than 6 months. The MEC was clear between +3° C. and 55° C. and the AM was clear between +3° C. and 45° C. for this period.

While the invention has been described with particular reference to certain embodiments thereof, it will be understood that changes and modifications may be made which are within the skill of the art. Accordingly, it is intended to be bound only by the following claims, in which:

What is claimed is:

1. An inert matrix composition for forming a clear, efficacious aqueous microemulsion upon admixture with a predetermined amount of a triazole fungicide and dilution water, which is stable at or below room temperature for an extended period of time, consisting essentially of:
  (i) a predetermined mixture of nonionic surfactants comprising:
    (a) about 5-30% of a $C_6$-$C_{18}$ alkylpyrrolidone;
    (b) about 5-30% of an alkyl phenol ethoxylated alcohol with an HLB $\geqq 6$; and
  an anionic surfactant comprising:
    (a') a metal salt of dodecylsulfate, dodecylbenzene sulfonate, dodecyltoluene sulfonate or lignin sulfonate, and
  (iii) about 5-40% water;
  (iv) up to 60% by weight of an N-alkyl($C_1$-$C_4$)pyrrolidone;
by weight of the composition.

2. An inert matrix composition according to claim 1 wherein (b) is a nonylphenol ethoxylated alcohol with 9 ethylene oxide groups.

3. An inert matrix composition according to claim 1 in which (a') is sodium dodecyl sulfate.

4. An inert matrix composition according to claim 1 in which the weight ratio of (a):(b):(a') is about 1: 1: 1.

5. An inert matrix composition according to claim 1 in which said N-alkyl($C_1$-$C_4$)pyrrolidone is N-methylpyrrolidone.

6. A two-part microemulsion system for forming a clear, efficacious, aqueous microemulsion of a triazole fungicide by admixture of the respective parts of said system, and dilution water, which is stable at or below room temperature for an extended period of time, consisting essentially of:
  (i) as the first part, the inert matrix composition of claim 1, and
  (ii) as the second part, a triazole fungicide, optionally including another active agricultural ingredient, selected from agricultural fertilizers, nutrients, plant growth accelerants, herbicides, plant growth controlling chemicals, insecticides, bactericides, fungicides, nematocides and fumigants;
wherein, optionally, said system includes up to 60% by weight of an N-alkyl($C_1$-$C_4$)pyrrolidone as cosolvent.

7. A system according to claim 6 in which said N-alkyl($C_1$-$C_4$)pyrrolidone is present in an amount of up to 60% in the first part of said system.

8. A microemulsion concentrate for forming a clear, efficacious aqueous microemulsion of a triazole fungicide upon dilution with water, which is stable at or below room temperature for an extended period of time, consisting essentially of:
  about 5-30% of a $C_6$-$C_{18}$ alkylpyrrolidone,
  about 5-30% of an alkyl phenol ethoxylated alcohol having an HLB$\geqq 6$,
  about 5-30% of a metal salt of dodecyl sulfate, dodecylbenzene sulfonate, dodecyltoluene sulfonate or lignin sulfonate,
  about 0-60% of an N-alkyl($C_1$-$C_4$)pyrrolidone, and
  about 1-25% of a triazole fungicide,
by weight of said concentrate.

9. A microemulsion concentrate according to claim 8 wherein said N-alkyl($C_1$-$C_4$)pyrrolidone is N-methylpyrrolidone which is present in an amount of about 5-60%.

10. A microemulsion concentrate according to claim 8 in which said triazole fungicide is penconazole.

11. A clear, efficacious, aqueous microemulsion of a triazole fungicide which is stable at or below room temperature for an extended period of time consisting essentially of the microemulsion concentrate of claim 8 diluted up to 200 times with water.

12. An aqueous microemulsion comprising about 0.5-20 parts of the microemulsion concentrate of claim 8, and about 80-99.5 parts of water.

13. An aqueous microemulsion according to claim 11 which includes up to about 60% of an N-alkyl ($C_1$-$C_4$)pyrrolidone.

14. An aqueous microemulsion according to claim 13 wherein said N-alkyl($C_1$-$C_4$)pyrrolidone is N-methylpyrrolidone.

15. An aqueous microemulsion according to claim 11 comprising:
  about 0.07% octylpyrrolidone,
  about 0.07% nonyl phenol ethoxylated alcohol with 9 EOs,
  about 0.07% sodium dodecyl sulfate,
  about 0.07% N-methylpyrrolidone,
  about 0.05% penconazole, and
  about 99.7% water.

* * * * *